US006542580B1

(12) United States Patent
Carver et al.

(10) Patent No.: US 6,542,580 B1
(45) Date of Patent: Apr. 1, 2003

(54) RELOCATABLE X-RAY IMAGING SYSTEM AND METHOD FOR INSPECTING VEHICLES AND CONTAINERS

(75) Inventors: James M. Carver, Cottage Grove, OR (US); Andreas F. Kotowski, Rancho Palos Verdes, CA (US)

(73) Assignee: Rapiscan Security Products (USA), Inc., Hawthorne, CA (US)

( * ) Notice: Subject to any disclaimer, the term of this patent is extended or adjusted under 35 U.S.C. 154(b) by 0 days.

(21) Appl. No.: 10/052,916

(22) Filed: Jan. 15, 2002

(51) Int. Cl.[7] .............................................. G01N 23/02
(52) U.S. Cl. ...................................................... 378/580
(58) Field of Search ............................ 378/57, 195–197

(56) References Cited

U.S. PATENT DOCUMENTS

| | | |
|---|---|---|
| 4,366,382 A | 12/1982 | Kotowski |
| 4,430,568 A | 2/1984 | Yoshida et al. |
| 4,599,740 A | 7/1986 | Cable |
| 5,065,418 A | 11/1991 | Bermbach et al. |
| 5,091,924 A * | 2/1992 | Bermbach et al. ............ 378/57 |
| 5,247,561 A | 9/1993 | Kotowski |
| 5,838,759 A | 11/1998 | Armistead |
| 5,910,973 A | 6/1999 | Grodzins |
| 6,192,104 B1 | 2/2001 | Adams et al. |
| 6,278,115 B1 | 8/2001 | Annis et al. |

* cited by examiner

*Primary Examiner*—Craig E. Church
(74) *Attorney, Agent, or Firm*—Jones Day

(57) ABSTRACT

A readily relocatable X-ray imaging system for inspecting the contents of vehicles and containers, and a method for using the same. In a preferred embodiment, the system is relatively small in size, and is used for inspecting containers and passenger vehicles, such as cars, SUVs, and small trucks, at a variety of sites. The X-ray inspection system includes a substantially rectangular frame having an X-ray imaging system disposed thereon. The frame is detachably connected to a conveyor mechanism having a minimal height, which allows drivers and passengers of vehicles to readily step off of and onto the conveyor mechanism without the aid of steps, railings, and the like. In a preferred configuration, the conveyor mechanism includes two detachable sections comprising a plurality of rollers, or other transport mechanism, having a radio-transparent plate or belt resting thereon for transporting a vehicle or container through the inspection area under the X-ray frame.

44 Claims, 9 Drawing Sheets

RELOCATABLE X-RAY IMAGING SYSTEM AND METHOD FOR INSPECTING VEHICLES AND CONTAINERS

FIELD OF THE INVENTION

The field of the invention generally relates to X-ray inspection systems used for security purposes. More particularly, the invention relates to a system and method for inspecting vehicles including passenger vehicles and light-load trucks.

BACKGROUND OF THE INVENTION

X-ray inspection systems have generally been used to inspect the contents of automobiles, trucks, rail cars, cargo containers, and other vessels of transport. Such systems are generally set up at airports, seaports, building entrances, border crossings, and other places where contraband, weapons, explosives, drugs, or other illegal items are likely to be found in transit. X-ray inspection systems are also often used to verify the contents of containers and vehicles, and to ensure the accuracy of shipping manifests and the like.

X-ray inspection systems for inspecting large objects are generally of the "fixed-site" variety, wherein vehicles or containers are brought to the inspection site to undergo X-ray imaging. Such systems commonly comprise a large inspection tunnel through which vehicles or containers are transported. The vehicles or containers are generally towed through the inspection tunnel, or are transported through the tunnel along a large conveyor mechanism.

As a vehicle or container is transported through the inspection tunnel, an X-ray imaging source generates an X-ray beam toward the vehicle or container. After the X-ray beam passes through, or penetrates, the vehicle or container, a detector receives the beam and produces an output signal representative of the vehicle or container, and of the contents located therein.

In many inspection systems, a plurality of signals representative of individual segments, i.e., successive cross-sections or "slices," of the vehicle or container may be transmitted, then summed together, to represent the entire vehicle or container. The output signal, or signals, is then converted into a visual image of the vehicle or container, and of the contents located therein, which is sent to a monitor or viewing screen so that the image may be viewed by an inspection system operator. The system operator may then determine whether any improper items are located inside the vehicle or container.

While fixed-site X-ray inspection systems have adequately performed in their particular implementations, the need has arisen for an X-ray imaging system that is readily relocatable and/or transportable to meet the needs of a given site or event, and that may be used to inspect smaller passenger vehicles, such as cars, SUVs, and small trucks. This is especially true given the threat that terrorism presents throughout the world, which has led to a need to inspect vehicles, containers, and other objects that may be carrying contraband, explosives, or other dangerous or illegal items, in a variety of settings and venues.

For example, there is now a stronger desire to inspect vehicles and containers at events where large numbers of people, celebrities, or politicians gather, such as television and music awards shows, at government buildings and convention centers, at professional and college sporting events, and at other places or events that attract large crowds. Current fixed-site X-ray inspection systems are not suited to meet this need, as they are unable to accommodate areas and events that are not located at, or do not take place near, the inspection sites themselves. Moreover, current fixed-site X-ray inspection systems are very expensive to construct and maintain.

In an attempt to resolve these problems, relocatable inspection systems have been developed that can be assembled and used at a variety locations to inspect large commercial vehicles and cargo containers. These systems, however, currently have many shortcomings. Specifically, existing relocatable X-ray inspection systems are extremely cumbersome to transport from one location to the next, and they generally require lengthy disassembling and assembling procedures. Furthermore, these systems generally require powerful machinery to load and unload their components onto and off of multiple transport trucks for relocation. Thus, significant time and expense are required to transport and assemble existing relocatable X-ray imaging systems. As a result, for a given site or event requiring such an inspection system, substantial notice must be given, and substantial money expended, to allow for the time and preparation required to transport and assemble the system. This, in turn, presents significant logistical problems where an event requiring security inspections occurs on short notice.

Additionally, existing relocatable X-ray inspection systems are generally designed for inspecting large trucks and cargo containers, not for inspecting passenger vehicles. As stated, the current systems are extremely cumbersome and time-consuming to relocate, and as such, are much larger than that which is required to inspect smaller passenger vehicles. Moreover, many of these existing systems have large conveyor platforms, which a vehicle driver may not readily step onto and off of without the aid of steps and/or railings.

In light of the above, a need exists for an X-ray imaging system used to inspect passenger vehicles that is readily relocatable, and flexible in terms of on-the-spot reconfiguration, such that a wide variety of site requirements can be met in a short amount of time and at minimal expense.

SUMMARY OF THE INVENTION

The present invention is generally directed to a low-cost, readily relocatable X-ray imaging system for quickly inspecting the contents of vehicles and containers, and a method of deploying and using the same. In a preferred embodiment, the system is relatively small in size compared to existing X-ray inspection systems, and is used for inspecting passenger vehicles, such as cars, SUVs, and light-load trucks, at various sites and venues.

In one aspect of the invention, the X-ray inspection system includes a substantially rectangular self-deploying frame having an X-ray source disposed thereon. The frame is attached to a conveyor mechanism having a minimal height, which allows drivers and passengers of vehicles to readily step out of and into their vehicles without the aid of steps, railings, and the like. Accordingly, a driver of a vehicle to be inspected may drive the vehicle onto one end of the conveyor mechanism, then exit the vehicle by stepping down from the vehicle onto the surface upon which the inspection system rests. The conveyor mechanism may then be activated to move the vehicle through the imaging area, or "inspection area," under the X-ray frame, so that a system operator may view the contents of the vehicle. If the system operator determines that the vehicle does not contain any improper items, the driver may move to the post-inspection end of the conveyor mechanism, step into the vehicle from the site surface, and drive away. If, on the other hand, the system operator determines that the vehicle may contain improper items, the operator may then detain the vehicle and physically inspect its contents.

In another aspect of the invention, the-conveyor mechanism comprises a plurality of rollers having one or more transport platforms resting thereon for transporting a vehicle or container through the inspection area. In use, a vehicle is driven onto the transport platforms. After the driver exits the vehicle, the conveyor mechanism is activated such that the transport platforms move across the rollers, thereby transporting the vehicle through the inspection area. After inspection, the driver may step into the vehicle from the site surface and drive away. The transport platforms are then moved back along the rollers to the first end of the conveyor mechanism so that they may receive the next vehicle to be inspected.

In another aspect of the invention, a method of deploying and using the X-ray inspection system is disclosed. An X-ray frame is deployed from a truck or other suitable transportation vehicle such that the X-ray frame lays flat on a surface. A winch mechanism on the frame is then activated to raise the X-ray frame along support poles, such that the frame is in a substantially vertical position. Two conveyor sections are then deployed from the vehicle and attached to opposing sides of the X-ray frame such that the two sections rest on the surface. One or more transport platforms may then be deployed from the transportation vehicle onto one of the conveyor sections. Imaging of vehicles may then take place as described above.

DETAILED DESCRIPTION OF THE PREFERRED EMBODIMENTS

The preferred embodiments will now be described with reference to the drawings. To facilitate description, any numeral identifying an element in one figure generally represents the same element when used in any other figure. The configurations shown in the figures are for illustrative purposes only, and are not intended to limit the scope of the invention.

A. Description of System Elements

Figure 1:
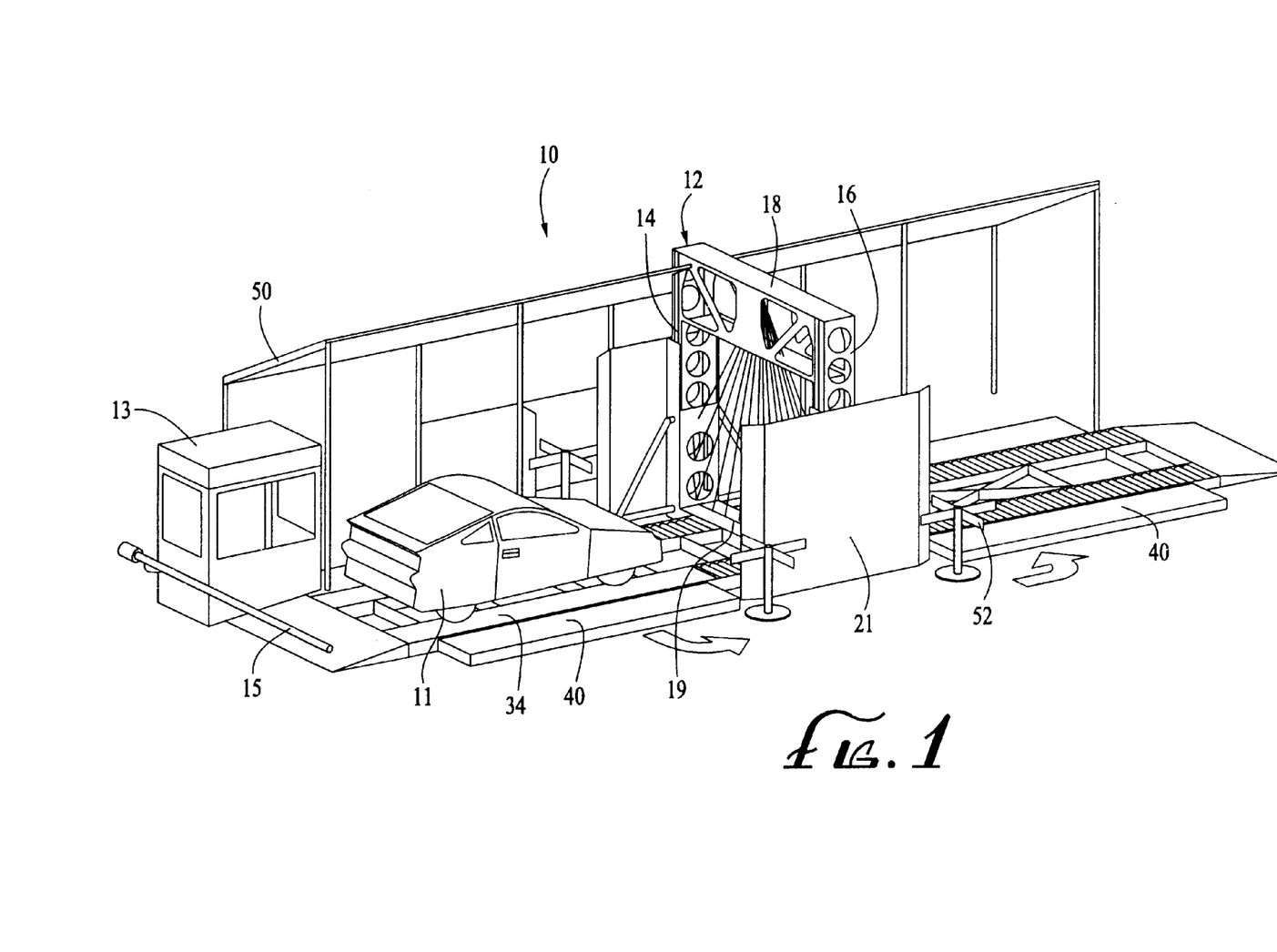
FIG. 1 is a perspective view of the relocatable X-ray inspection system of the current invention set up at an inspection site with a selection of covers and awnings removed for clarity.
Figure 2:
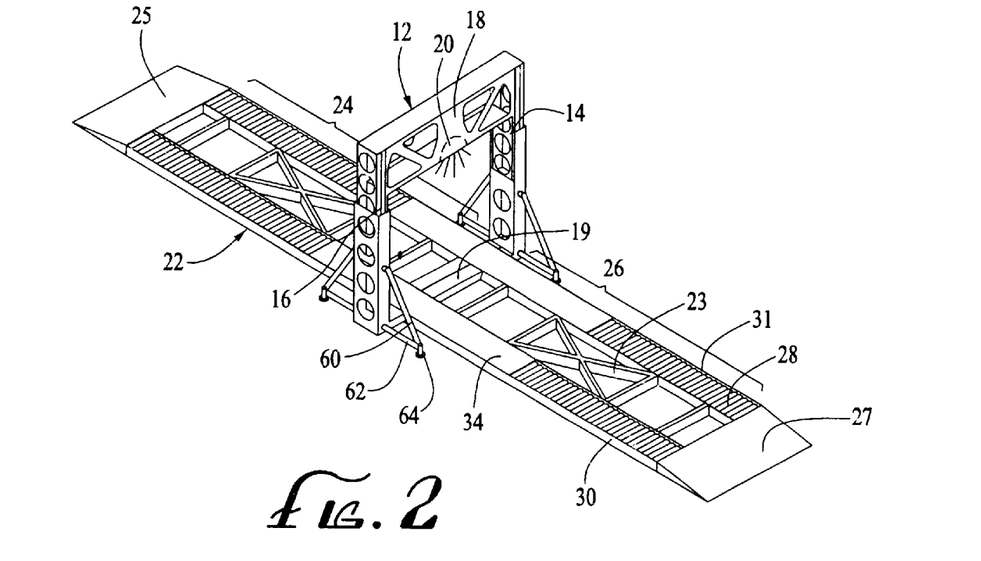
FIG. 2 is a perspective view of the relocatable X-ray inspection system of the current invention in isolation.

FIGS. 1 and 2 are perspective views of a relocatable X-ray inspection system 10. The inspection system 10 may be used for inspecting vehicles, containers, and other objects capable of concealing contraband, weapons, and the like. The inspection system 10 is preferably used for inspecting cars, vans, SUVs, light-load trucks, and other passenger vehicles, at various sites and events such as border crossings and entrances to government buildings. For ease of description, X-ray imaging of a vehicle 11 will be described herein, but it is to be understood that the inspection system 10 may also be used to inspect other containers and objects capable of concealing items.

FIG. 1 shows the inspection system 10 set up at an inspection site with an operator cabin 13, having a raisable gate 15 connected thereto, positioned at an entrance to the inspection system 10. The operator cabin 13 preferably contains all of the controls necessary for a system operator to manage and oversee the X-ray inspection process. The cabin 13 preferably contains a monitor for displaying X-ray images of objects and materials contained within a vehicle 11 being inspected, controls for raising and lowering the gate 15, an intercom system for communicating with vehicle drivers, and other controls for operating the various elements of the X-ray inspection system 10, as further described below.

The inspection system 10 includes a substantially rectangular frame 12, preferably made from rigid structural steel or any other suitable sturdy material. The frame 12 preferably comprises a first substantially vertical leg section 14 and a second substantially vertical leg section 16, each of which may comprise one or more segments, as further described below. The first leg section 14 is preferably spaced apart from the second leg section 16 by a distance that is greater than a width of the widest vehicle intended for inspection by the inspection system 10. In a preferred configuration, the first and second leg sections 14, 16 are spaced apart by approximately 10 to 12 feet, such that the inspection system 10 may accommodate vehicles having a width of up to approximately nine feet.

The first and second leg sections 14, 16 are preferably connected to one another by an X-ray generator section 18 and a base section 19, each of which may be integral with the leg sections 14, 16. The area underneath the X-ray generator section 18 and between the first and second leg sections 14, 16 defines an "inspection area" wherein vehicles undergo X-ray imaging. The base section 19 of the frame 12 preferably has a substantially level bottom face for resting on the inspection site surface, which may be the ground, a road, a parking lot, or any other substantially uniform surface.

Stabilizing struts 60 and support bars 62, or other suitable support structures, may preferably be connected to both sides of the first and second leg sections 14, 16 for maintaining the frame 12 in an upright position during vehicle inspection. The support bars 62 preferably have footpads 64 disposed thereon that rest on the inspection site surface and maintain the X-ray frame 12 in a stable, level position, as further described below.

The frame 12 preferably includes a drive gear, or other suitable drive mechanism, disposed therein. The drive gear may preferably be turned on and off with buttons, levers, switches, or any other suitable activation mechanism located on the frame 12. For ease of description, buttons will be described herein, but it is to be understood that levers, switches, or any other suitable activation mechanism may be used to activate the drive gear.

Figures 6A, 6B, 6C:
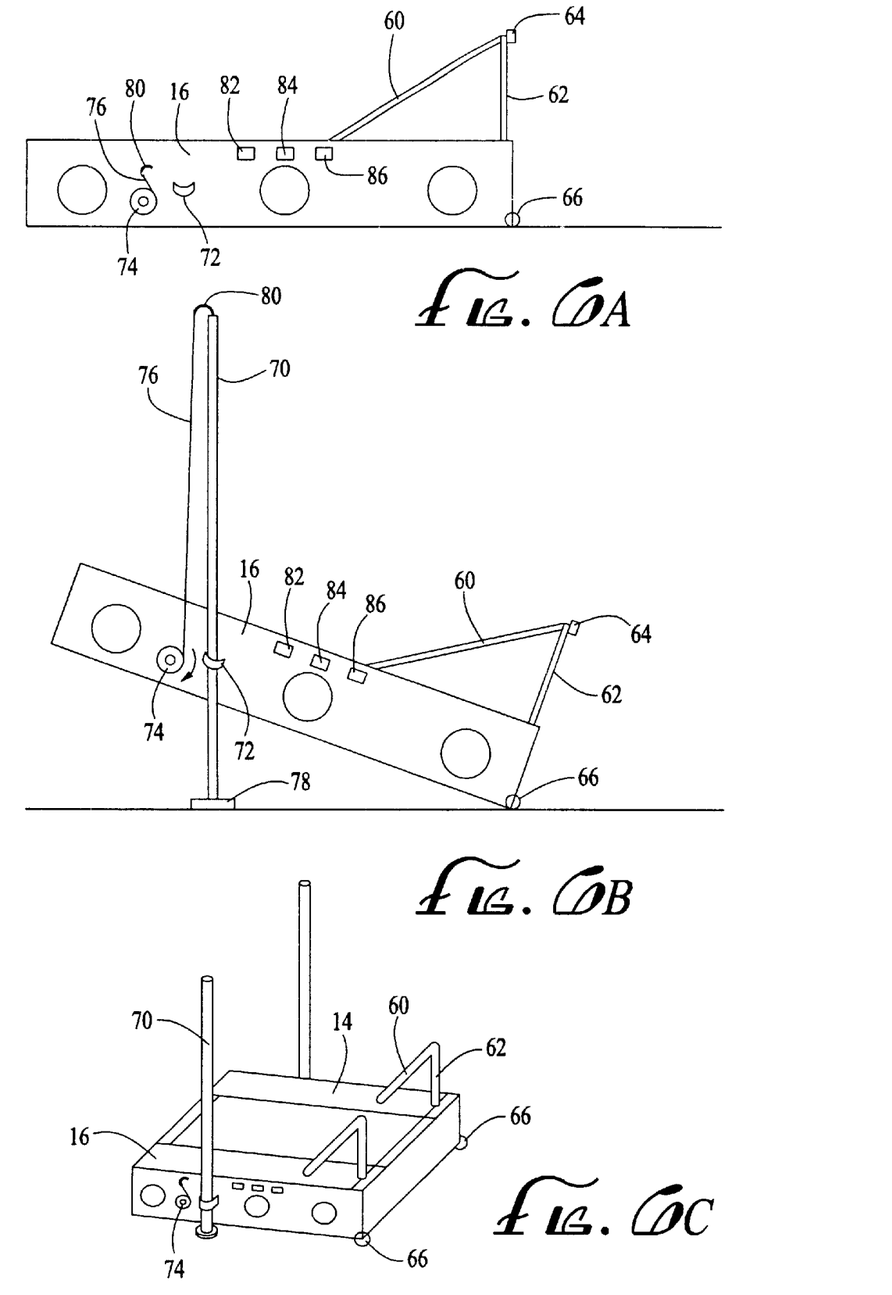
FIG. 6A is a side view of an X-ray frame at rest before being raised into an imaging position according to a preferred embodiment of the current invention.
FIG. 6B is a side view of the X-ray frame of FIG. 6A being raised into an imaging position.
FIG. 6C is a perspective view of the X-ray frame of FIG. 6A with support rods secured thereto.

As illustrated in FIGS. 6A–6C, the drive gear is preferably used to activate one or more winch mechanisms 74, such as pulley systems or other lifting mechanisms, which are optimally disposed on an outward facing surface of each of the first and second leg sections 14, 16 of the frame 12. Each winch mechanism 74 preferably has a cable or chain 76 wrapped therearound, the cable preferably having a hook 80, or other suitable connecting structure, located at a free end thereof. When the winch mechanisms 74 are activated, they preferably hoist the frame 12 up along jack rods 70 (as shown in FIGS. 6A and 6B), or any other suitable support rods, such that the frame 12 stands in a substantially upright position, as further described below.

The drive gear may also preferably be used to extend and retract the first and second leg sections 14, 16, such that the frame 12 may be collapsed for transport from location to location, as further described below. To accomplish this objective, each leg section 14, 16 may comprise two segments that are slidably connected to one another, or each leg section 14, 16 may slidably engage an upstanding segment of the base section 19, such that the segments may slide relative to one another. Alternatively, the first and second. leg sections 14, 16 may each be arranged in a telescoping configuration to provide height adjustment.

Figure 3:
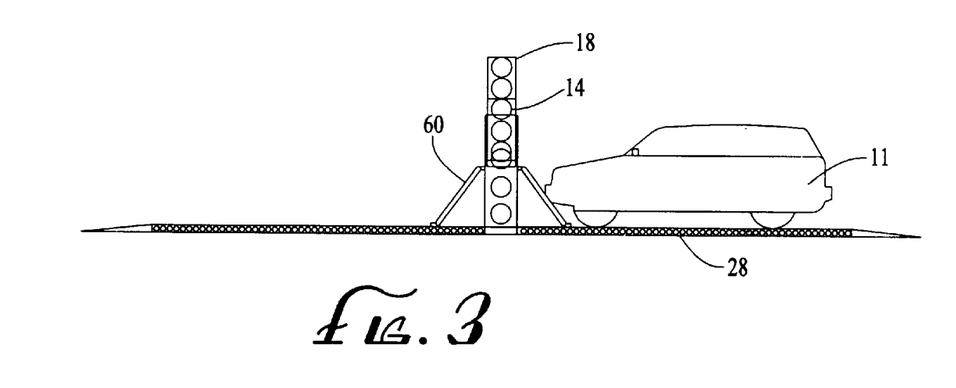
FIG. 3 is a side-sectional view of the relocatable X-ray inspection system of the current invention with a vehicle located thereon for inspection.
Figure 4:
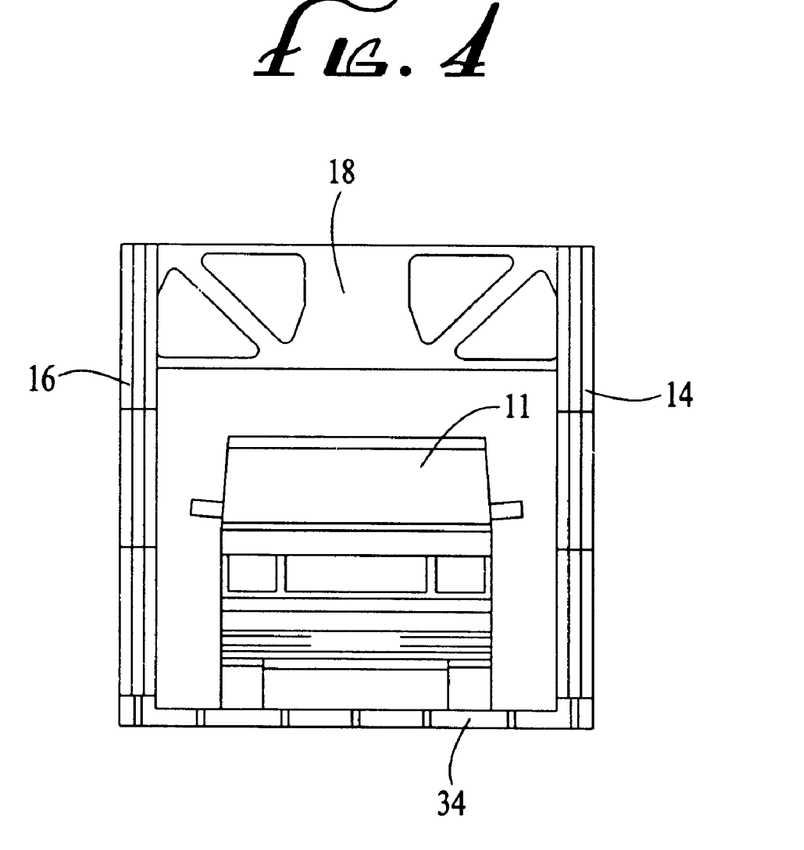
FIG. 4 is a front-sectional view of the relocatable X-ray inspection system of the current invention with a vehicle located thereon for inspection.

For vehicle inspection, the first and second leg sections 14, 16 are preferably extendable to an imaging height of approximately 12 to 13 feet, such that a clearance height of approximately 9 to 10 feet is provided between the X-ray generator section 18 and the base section 19, as shown in FIGS. 3 and 4. As a result, a passenger vehicle 11 or light-load truck may readily pass under the X-ray generator section 18 through the inspection area. During imaging of a vehicle, the first and second leg sections 14, 16 are preferably extended to their full imaging height, such that detectors on the frame 12 may properly detect X-ray beams produced by the system 10, as further described below.

For transport to and from an inspection site, the first and second leg sections 14, 16 may preferably be retracted to a height of approximately 6 to 8 feet, such that a wide load permit is not required to transport the frame 12 when the frame is positioned width-wise on a delivery vehicle (wide load permits are generally required for objects having a width greater than eight feet). Additionally, by reducing the height of the frame 12, the required size of the delivery truck may be minimized.

The X-ray generator section 18 preferably comprises a beam section oriented substantially perpendicular to the first and second leg sections 14, 16. The X-ray generator section 18 preferably includes an X-ray source 20 disposed thereon for generating an X-ray beam toward the vehicle 11 as it passes through the inspection area.

The X-ray source 20 may be any suitable X-ray beam generator, such as a radioisotopic source, an X-ray tube, or an electron beam accelerator. Suitable radioisotope sources include Cesium 137 and Cobalt 60. X-ray tubes with accelerating potentials of 20 keV to 500 keV are generally available. Electron beam accelerator sources such as linear accelerators are available with energies from approximately 1 MeV to 9 MeV and higher.

The X-ray source 20 preferably produces a curtain or fan of X-rays so that the vehicle may be imaged one cross-section or "slice" at a time as it passes through the inspection area. The individual slices may then be summed together to produce an X-ray image of the entire vehicle and its contents. An example of an X-ray inspection system utilizing a fan-shaped X-ray beam is disclosed in U.S. Pat. No. 4,366, 382 to Kotowski, which is herein incorporated by reference.

A suitable collimator mechanism may preferably be used to narrow and limit the projected beam into a fan of dimensional beams necessary to illuminate detectors in the system 10, as further described below. The collimator mechanism also preferably reduces scattered radiation by reducing the total amount of X-rays emitted during vehicle inspection. As a result, a reduced amount of shielding is required to protect the system operator and the vehicle drivers and passengers.

In an alternative embodiment, the X-ray beam may be collimated to a flying spot, as opposed to a fan, that moves in a line across one or more detectors (detector configurations are further described below). Such a configuration effectively creates a line camera, which produces images of an object in sections that may be summed together to produce an image of the entire object and its contents. The X-ray beam may alternatively be a pencil-beam, a cone-shaped beam, or any other beam suitable for X-ray imaging. Thus, the fan-shaped beam will be described herein by way of example only.

The radiation produced by the inspection system 10 is preferably maintained at a relatively minimal level compared to the radiation produced by larger fixed-site tunnel systems. This is preferred because the open configuration of the inspection system 10 may allow some scattered radiation to reach a system operator and/or vehicle passengers, which could endanger their health if the radiation produced is at high concentrations. Thus, X-ray beams are preferably produced in the range of 100 keV to 500 keV to minimize this risk.

To further alleviate the danger caused by scattered radiation, radiation shields 21 may be positioned adjacent to the first and second leg sections 14, 16 to prevent radiation from escaping the inspection area, as shown in FIG. 1. Additionally, the X-ray source 20 preferably generates X-ray beams substantially downward, such that the ground may absorb much of the radiation produced. As a result, scattered radiation in the inspection system 10 is substantially reduced.

A first detector array (not visible in the figures) is preferably disposed on or within the base section 19 of the frame 12, such that the first detector array faces generally upward for detecting rays of the X-ray beam that travel substantially downward. Additional detector arrays are preferably disposed on or within the first and second leg sections 14, 16 of the frame 12 for detecting rays of the X-ray beam that do not travel substantially downward, such as those rays that are used for imaging the upper portions of a tall vehicle, such as an SUV. By placing detectors on both the base section 19 and the leg sections 14, 16 of the frame 12, an X-ray image of an entire vehicle and its contents may be produced by the inspection system 10.

Each detector array preferably comprises a linear array of detectors, such as photodiodes, which absorb the X-ray beams transmitted through the vehicle being inspected and convert the absorbed X-ray beams into radiographic signals representative of the vehicle and of materials contained therein. Alternatively, an area detector, such as a scintillating strip or other suitable detector, may be used to detect the X-ray beams that pass through the vehicle, and to convert the beams into representative radiographic signals.

The signals produced by the detectors may preferably be sent to a suitable image producing mechanism, such as a system processor, via cables, wires, or other suitable means. Alternatively, the image producing mechanism may receive the detector signals remotely, such that no wires or cables are required. The image producing mechanism preferably converts the detector signals into visual images of the vehicle and of materials contained therein, which may be viewed on a monitor (or other viewing mechanism) by the system operator.

In a preferred embodiment, the X-ray inspection system 10 is equipped with dual energy imaging capabilities. Dual energy imaging is a process wherein X-ray beams are produced by an X-ray source at multiple radiation energy levels, with one component preferably below 100 keV, and at least one other component preferably above 100 keV, to identify and distinguish between different types of matter. A first detector element is preferably positioned opposite the X-ray source to receive and respond predominantly to X-ray beams in the lower energy range, while the remaining X-ray beams, being generally of higher energy, pass through the first detector element. A second detector element is preferably positioned to receive and respond to the higher energy radiation passing through the first detector element.

A filter element may be interposed between the detector elements to enhance discrimination in the energy response of the respective detector elements. The different detector elements preferably produce separate and simultaneous signals representing patterns of relatively lower and higher energy emergent from a vehicle. Digital data processing and conversion equipment may then use these signals to produce distinctive digital information representative of each of the images inside the vehicle.

For example, color-encoded images may be produced wherein organic, inorganic, and metallic materials located inside a vehicle appear as different colors on a video monitor, such that a system operator may readily distinguish these materials from one another. Thus, by utilizing dual energy imaging in the inspection system 10, the system operator may more easily identify improper materials located inside the vehicle. Dual energy imaging may be particularly effective in the inspection system 10 due to the reduced amount of scattered radiation, which may otherwise interfere with optimal dual energy imaging performance, produced as a result of ground absorption.

The frame 12 of the X-ray inspection system 10 is optimally connected to a light-weight conveyor mechanism 22. The conveyor mechanism 22 may be similar in construction to a gravity roller conveyor, and preferably has a substantially flat base portion for resting on a site surface, such as a road, a parking lot, or other suitable surface.

The conveyor mechanism 22 preferably includes a first conveyor section 24 and a second conveyor section 26, which may be detachably connected to opposite sides of the base section 19 of the frame 12. The two conveyor sections 24, 26 may be connected to the base section 19 via hooks, bolts, interlocking portions, and/or any other suitable connecting means. Hooks are preferably used, however, so that the conveyor sections 24, 26 may slide off of a delivery vehicle and readily hook onto the base section 19, as further described below.

An ingress ramp 25 and an egress ramp 27 may be connected to the first and second conveyor sections 24, 26, respectively, to facilitate vehicles driving onto and off of the conveyor mechanism 22. The ramps 25, 27 may be detachably connected to the conveyor sections 24, 26 via hooks, or any other suitable connecting means, or may be hingedly connected thereto, such that the ramps 25, 27 may be folded against the conveyor sections 24, 26 during transport. The ramps 25, 27 may each comprise one solid unit, as illustrated in FIG. 2, or may each comprise two separate ramp sections that are spaced apart by a distance generally corresponding to the spacing of tires on a passenger vehicle or light-load truck.

Each conveyor section 24, 26 preferably includes a substantially U-shaped support section having parallel leg portions 30, 31, which are also preferably spaced apart by a distance generally corresponding to the spacing of tires on a passenger vehicle or light-load truck. Support beams 23 may be disposed between the leg portions 30, 31 to provide structural support to the conveyor mechanism 22. Each leg portion 30, 31 preferably has a width substantially greater than a standard vehicle tire such that a wide range of vehicles may be accommodated by the leg portions 30, 31.

As illustrated in FIG. 2, each leg portion 30, 31 preferably includes a plurality of successively arranged rollers 28 disposed thereon. In an alternative embodiment, each conveyor section 24, 26 may comprise a substantially rectangular base section having a plurality of rollers disposed across a width thereof. The rollers may comprise any material suitable for supporting the weight of a large passenger vehicle, such as aluminum or steel.

Alternatively, other methods of transport, such as towing vehicles on their tires with a 'car wash' type mechanism, or using an air bearing support, a conveyor belt, or segmented plate conveyors, may be used to move vehicles through the inspection area. Thus, the roller configuration will be described herein by way of example only, and is not intended to limit the possible methods of vehicle transport through the inspection area.

The conveyor mechanism 22 preferably includes one or more transport platforms 34, which rest on the plurality of rollers 28. In the U-shaped support section configuration, as illustrated in FIGS. 1–4, a transport platform 34 preferably rests on the rollers 28 of each respective leg portion 30, 31. As illustrated in FIGS. 1 and 4, the transport platforms 34 are preferably used for supporting and transporting a vehicle 11 resting thereon. The transport platforms 34 are preferably movable along the rollers 28 of the first and second conveyor sections 24, 26 in two directions through the inspection area.

The transport platforms 34 are preferably made of a radio-transparent material through which radiation from X-ray beams may pass such that the radiation may be primarily absorbed by the ground. The transport platforms may comprise carbon fiber (epoxy) composite, fiberglass/epoxy composite, aluminum plating, thin steel plate, or any other suitable radio-transparent material.

The first detector array is preferably relatively thin such that the base section 19 of the frame 12 may have substantially the same height as the conveyor mechanism 22, thereby providing a relatively smooth transition between the conveyor sections 24, 26 and the base section 19. As a result, the transport platforms 34 may move smoothly across the base section 19 during inspection of vehicles.

An activation mechanism (not visible in the figures), such as a chain mechanism, belts, gears, cranks, or a controlled vibration mechanism, may preferably be connected to the rollers 28 for providing rotating motion to the rollers 28 in both clockwise and counterclockwise directions. The activation mechanism is preferably controlled by the system operator, and may preferably be electronically activated by any suitable means. When the activation mechanism is activated, the rollers 28 rotate in the chosen direction, thereby causing the transport platforms 34 to move along the rollers 28 in a direction tangent to the direction of rotation of the rollers 28. Accordingly, a vehicle resting on the transport platforms 34 may be transported along the rollers 28 over the length of the conveyor mechanism 22.

The conveyor mechanism 22 preferably has a relatively minimal height such that drivers (and passengers) may readily step into and out of their vehicles without the aid of steps or railings. In a preferred embodiment, pedestrian platforms 40, which preferably have a height substantially equal to that of the conveyor mechanism 22, may be placed on the site surface adjacent to the conveyor mechanism 22 to allow vehicle passengers to step out of their vehicles onto the platforms 40. The passengers may then step onto the site surface, without the aid of steps or railings.

It is possible to reduce the height of the conveyor mechanism 22, because the described roller configuration requires much less vertical space than that required by conveyor mechanisms utilized in existing inspection systems, which are generally designed to transport and support heavy commercial trucks and large cargo containers. Due to the substantial structural support required to construct the conveyor mechanisms used in such systems, the height of the conveyors is generally too great to allow a person to readily step off of and onto the conveyors without the aid of steps and/or railings.

The height of the conveyor mechanism 22 of the inspection system 10, on the contrary, permits a person to readily step off of and onto the conveyor mechanism 22. Each of the rollers 28 disposed on the first and second conveyor sections 24, 26 of the conveyor mechanism 22 preferably has a diameter ranging from 1 to 8 inches. Each conveyor section 24, 26, in turn, has a height ranging from approximately 1 inch to 2 feet, preferably from 2 to 10 inches, although other dimensions may be utilized. Thus, when exiting a vehicle located on the conveyor mechanism 22, a driver may step out of the vehicle onto the pedestrian platforms 40, and then step down a short distance onto the ground, or may step directly onto the ground from the vehicle, without the aid of steps or railings. This reduces cost and logistical issues, and increases inspection speed, because, without steps or railings, fewer parts are required, and drivers may more quickly enter and exit their vehicles.

B. Description of the Deployment and Relocation Processes

The X-ray inspection system 10 is preferably readily deployable and collapsible, so as to reduce the time and effort involved in moving the system 10 from one inspection site to another. A delivery vehicle, which may be an inclined flatbed truck similar to a car-carrier style tow truck, or any other suitable transport vehicle, is preferably used to transport the inspection system 10 from one location to the next. The first and second conveyor sections 24, 26, which are detachable from the X-ray frame 12, may preferably be stacked on top of one another on the delivery vehicle. The X-ray frame 12 may then be placed on top of or next to the conveyor sections 24, 26 on the delivery vehicle.

A cable winch, or other suitable lifting mechanism, may be used to lift the various components of the inspection system 10 onto the delivery vehicle. The conveyor sections 24, 26 preferably readily load onto the delivery vehicle via the rollers 28 disposed thereon, which provide rolling movement to the conveyor sections 24, 26 as they are pulled up the inclined bed of the delivery vehicle by the winch system. The conveyor sections 24, 26 may preferably be individually locked into place on the bed of the delivery vehicle via locking levers or other suitable locking mechanisms, as further described below. The X-ray frame 12 may be pulled up onto the conveyor sections 24, 26 via the cable winch, in a manner similar to a car being pulled onto a flatbed car-carrier. The X-ray frame 12 may be provided with a plurality of wheels on one face of each of the first and second leg sections 14, 16 to facilitate loading the frame 12 onto the delivery vehicle in this manner.

Figure 5:
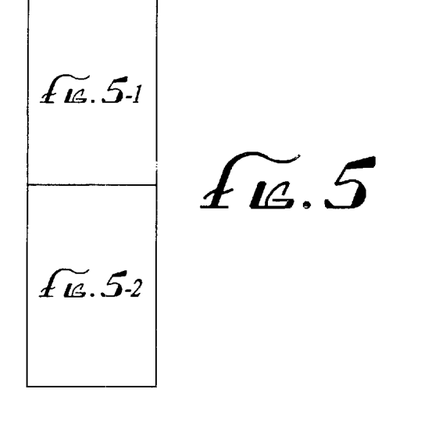
FIG. 5 is a flowchart illustrating a preferred process for deploying the relocatable X-ray inspection system of the current invention at an inspection site.

When the delivery vehicle arrives at an inspection site, the following procedures may preferably be followed to assemble the inspection system 10, as outlined in the flowchart of FIG. 5. The bed of the delivery vehicle is preferably raised to an inclined position such that the X-ray frame 12 slides off of the vehicle onto the site surface, which may be the ground, a road, or other firm surface. The frame 12 is preferably arranged such that it slides off of the delivery vehicle onto the site surface in a position in which the frame 12 lies flat on a front or rear face of the X-ray generator section 18 and of the first and second leg sections 14, 16.

An operator may then connect the stabilizing struts 60 and the support bars 62 to the upward facing side of the first and second leg sections 14, 16 via a locking mechanism, hooks, bolts, screws, or any other suitable fastening means. Each stabilizing strut 60 may then be connected to its respective support bar 62, such that the stabilizing strut 60 and the support bar 62 form a triangle shape with the leg section to which they are connected, as illustrated in FIGS. 2, 3, and 6A–6C.

Alternatively, the stabilizing struts 60 and support bars 62 may be hingedly connected to the upward facing side of the first and second leg sections 14, 16, such that they may be locked into a stabilizing position after the frame 12 is deployed, and closed into a storage position for transport. In such an embodiment, the stabilizing struts 60 and support bars 62 preferably remain attached to the first and second leg sections 14, 16 at all times, and therefore do not have to be connected and disconnected each time that the inspection system 10 is relocated.

Once the stabilizing struts 60 and support bars 62 are connected to the upward facing side of the first and second leg sections 14, 16, the operator preferably slides a pair of jack rods 70, or other suitable support rods, through a pair of guide structures 72 that are preferably connected to the outward facing surfaces of the first and second leg sections 14, 16. The guide structures 72 are preferably pivotally connected to the leg sections 14, 16 so that they may pivot as the frame 12 is being raised into an upright position, as further described below. Each jack rod 70 may preferably be inserted into a base section 78 that rests firmly on the inspection site surface and provides additional support during the frame-raising process.

After the jack rods 70 are inserted, the operator preferably extends the cable 76 from each winch mechanism 74 to a length that permits the cable 76 to reach the top of the corresponding jack rod 70. The operator then preferably hooks the hook 80 at the free end of each cable 76 over a bar, or into an opening, at the top of the corresponding jack rod 70.

Once the cables 76 are hooked onto the top of the jack rods 70, the operator preferably presses a first button 82, or other activation mechanism, located on the frame 12 to activate the drive gear, which in turn, activates the winch mechanisms 74. Referring to FIGS. 6A and 6B, the winch mechanism 74 on the second leg section 16 is illustrated, although it is to be understood that both winch mechanisms 74 preferably perform in substantially the same manner.

The winch mechanism 74 turns in a clockwise direction and pulls the cable 76 so that it is taut. As the winch mechanism 74 continues to turn, the length of the cable 76 is reduced, and the frame 12 accordingly begins to rise, as shown in FIG. 6B. A roller mechanism 66, such as a plurality of wheels, a rolling tube, or any other suitable rolling device, may preferably be disposed on the base section 19 of the frame to provide rolling movement to the frame 12 along the site surface as the frame 12 is raised into an imaging position.

The frame 12 continues to rise until it is in a substantially upright position, in which only the foot pads 64 of the support bars 62 preferably touch the site surface. Once the frame 12 reaches this point, the operator preferably hits the first button 82 to stop the drive gear. In this position, the base section 19 of the frame is preferably suspended above the surface by a small distance, so that the operator may readily attach the stabilizing struts 60 and support bars 62 to the other side of the first and second leg sections 14, 16, in a manner similar to that which was used to attach the first set of stabilizing struts 60 and support bars 62.

After the operator attaches the second set of stabilizing struts 60 and support bars 62 to the first and second leg sections 14, 16, the operator preferably hits a second button 84, or other activation mechanism, on the frame 12 that causes the drive gear to turn the winch mechanisms 74 in the opposite direction from that which they turned to raise the frame 12. Accordingly, the base section 19 of the frame 12 is lowered to the site surface, at which point the operator may hit the second button 84 to deactivate the drive gear. At this point, the stabilizing struts 60 and support bars 62 preferably maintain the frame 12 in an upright, level position.

The operator may then unhook the cables 76 from the jack rods 70, and slide the jack rods out of the guide structures 72. The jack rods may then be placed into the delivery vehicle, or any other convenient location, such that they are accessible for lowering the frame 12 onto its face when it is time to move the frame to another inspection site, as further described below. The operator may also preferably activate the drive gear to wind up the slack portion of the cables 76, such that they do not interfere with the inspection process.

After the frame 12 is stabilized, the operator may then hit a third button 86, or other activation mechanism, on the frame 12 to activate the drive gear, which extends the first and second leg sections 14, 16 to a desired imaging height. As described above, the desired imaging height is preferably approximately 12 to 13 feet, which allows vehicles to readily pass under the X-ray generator section 18 of the frame 12.

Once the frame 12 is erected, the operator preferably deploys the first and second conveyor sections 24, 26 from the delivery vehicle, one at a time, to either side of the frame 12. The conveyor sections 24, 26 preferably connect to the base section 19 as they are fed off of the truck platform. To accomplish this objective, the operator preferably aligns the rear of the delivery vehicle with the base section 19 of the frame 12, and detaches the first conveyor section 24 from the vehicle via controls located inside the vehicle. The first conveyor section 24 then slides down the inclined truck platform and connects to the base section 19, via hooks or any other suitable connecting means.

The operator may then drive the vehicle away from the frame 12 such that the remainder of the first conveyor section 24 slides down the truck platform and lays flat on the ground. Once the first conveyor section 24 is connected to the base section 19 of the frame 12, the operator may then drive the delivery vehicle around to the other side of the frame 12 and deploy the second conveyor section 26 in a manner similar to that used to deploy the first conveyor section 24.

The transport platforms 34 may preferably be resting on one of the conveyor sections 24, 26 when the conveyor sections 24, 26 are deployed, or may be lowered from the vehicle onto the rollers 28 of the conveyor mechanism 22 after the conveyor mechanism 22 is assembled. The transport platforms 34 may be lowered manually, or by a suitable control cable mechanism located on the delivery vehicle, or may be deployed in a manner similar to that in which the conveyor sections 24, 26 were deployed.

The ingress ramp 25 and the egress ramp 27 may then be deployed and attached to the first and second conveyor sections 24, 26, respectively. The ramps 25, 27 may also be deployed manually, or by a suitable control cable mechanism located on the delivery vehicle, or in a manner similar to that in which the conveyor sections 24, 26 were deployed. Alternatively, in the embodiment wherein the ramps 25, 27 are hingedly attached to the first and second conveyor sections 24, 26, the ramps may be pivoted outwardly from the conveyor sections 24, 26 until the ramps 25, 27 come to rest on the site surface.

The delivery vehicle and/or the operator may further deploy any desired site accessories, such as awnings 50, turnstiles 52, radiation shields 21, an operator cabin 13, and/or any other suitable items, from the delivery vehicle. To accomplish this objective, a control cable mechanism, or other suitable deployment mechanism, may be located on the delivery vehicle for deploying the desired accessories. The deployment mechanism may preferably be operated via controls located on the outside of, or inside the cab of, the delivery vehicle.

The operator may then connect any electrical cables and/or wires leading from the monitoring equipment, which is preferably located inside the operator cabin 13, to the detector array on the X-ray frame 12. The cables and/or wires are preferably used for transmitting signals produced by the detectors to an image processor, or other suitable image-producing mechanism, which provides a visual image of the vehicle and of contents located therein on the monitoring equipment. Alternatively, the detector array may produce output signals that are picked up remotely by the image processor, in which case no cables or wires are required.

When the inspection system 10 is no longer required at a given site, the components of the inspection system 10, and its accessories, may preferably be loaded onto the delivery vehicle in substantially the opposite order in which they were deployed. The first and second conveyor sections 24, 26 may preferably be detached from the base section 19 of the frame by the operator, and then pulled up onto the bed of the delivery vehicle by the cable winch disposed thereon, as described above.

The operator may then activate the drive gear to lower the first and second leg sections 14, 16 to their transport height, which is preferably from 6 to 8 feet, as explained above. Once the leg sections 14, 16 are lowered, the operator may slide the jack rods 70 through the guide structures 72 on the first and second leg sections 14, 16, and hook the cables 76 from the winch mechanisms 74 to the top of the jack rods 70. The operator may then activate the winch mechanism 74 to raise the frame 12 slightly off of the site surface.

While the base section 19 of the frame 12 is raised off of the site surface, the operator may remove the stabilizing struts 60 and support bars 62 from one side of the first and second leg sections 14, 16. The operator may then activate the winch mechanism 74 to lower the frame 12 to the site surface, such that the frame 12 lies on its face from which the stabilizing struts 60 and support bars 62 were removed.

Once the frame 12 is lying flat on the site surface, the operator may remove the stabilizing struts 60 and support bars 62 from the other side of the frame 12. The frame 12 may then be hooked up to the cable winch located on the delivery vehicle, and the cable winch may be activated to load the frame 12 onto the delivery vehicle.

After the frame 12 and the conveyor sections 24, 26 are loaded onto the delivery vehicle, the control cable mechanism may be used to load the various other site accessories onto the delivery vehicle. Once all of the system components are loaded onto the delivery vehicle, the vehicle may be driven to the next inspection site, or to a storage facility where the inspection equipment may be stored.

In an alternative embodiment, the rollers 28 of the first and second conveyor sections 24, 26 may be powered by batteries, electricity, or any other suitable energy source, such that the conveyor sections 24, 26 may self-load onto, and self-unload off of, the delivery vehicle. Additionally, the frame 12 may be powered and provided with wheels, such that the frame 12 may self-load onto, and self-unload off of, the delivery vehicle. In such an embodiment, the bed of the delivery vehicle may be aligned with the component to be loaded, and the component may then be activated to power itself up the inclined bed. Alternatively, one or more of the components may be controlled remotely by a handheld device, or by controls located on or inside the delivery vehicle.

C. Description of the Inspection Process

Figure 7:
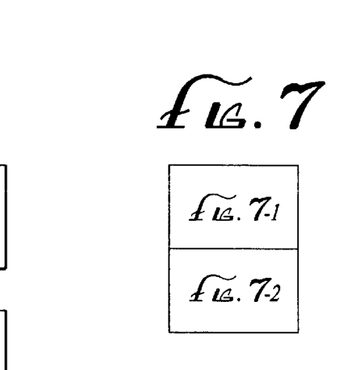
FIG. 7 is a flowchart illustrating a preferred inspection process utilizing the relocatable X-ray inspection system of the current invention.

FIG. 7 is a flowchart illustrating a preferred inspection process that may be utilized with the inspection system 10. Once the inspection system 10 is assembled, vehicle inspection may begin. To begin the inspection process, a vehicle is driven onto the conveyor mechanism 22. The vehicle is preferably driven onto the transport platforms 34, which rest on the rollers 28 of the first conveyor section 24. The vehicle may be driven onto the transport platforms 34 by the vehicle driver, or by the system operator. To maximize the speed of the inspection process, however, it is preferable to have the vehicle driver drive the vehicle onto the transport platforms 34 so that the system operator may remain in the operator cabin 13.

A gate 15, which the operator may raise electronically from inside the operator cabin 13, is preferably connected to the operator cabin 13 at or near the entrance to the inspection system 10. When the system 10 is ready to inspect a vehicle, i.e., when the previous vehicle has completed the inspection process and exited the conveyor mechanism 22, the operator may raise the gate to allow the next vehicle to drive up the ingress ramp 25 onto the conveyor mechanism 22. The gate 15 may then be lowered by the operator, or lowered automatically once the vehicle clears the reach of the gate 15, to prevent additional vehicles from entering the inspection system 10.

Once the vehicle comes to rest on the transport platforms 34, the vehicle driver preferably turns the vehicle off and exits the vehicle. An additional gate, not shown in the figures, may be positioned to prevent the driver from driving the vehicle off of the transport platforms 34 and onto the rollers 28. To exit the vehicle, the driver (and any other passengers) may step onto the pedestrian platforms 40, and then step down onto the ground, or may step directly onto the ground from the vehicle, without the aid of steps or railings, due to the reduced height of the conveyor mechanism 22.

The driver may then walk along the outside of the inspection system 10 and stand near the second conveyor section 26 to await delivery of the vehicle after it undergoes the inspection process, in a manner similar to that of a person having his/her bags scanned at an airport. To facilitate this process, the operator cabin 13 is preferably provided with an intercom system that allows the operator to communicate instructions to the driver regarding where and how the driver should proceed. Warning signs and the like may also preferably be posted at the inspection site informing the driver of where it is safe and unsafe to stand or sit during the inspection process.

After the driver is safely out of the vehicle, the operator may activate the activation mechanism to rotate the rollers 28, which move the transport platforms 34, and the vehicle located thereon, toward the inspection area. As the transport platforms 34 move across the base section 19 of the X-ray frame 12, the vehicle begins to pass through the inspection area, and an X-ray beam is generated from the X-ray source 20. The X-ray beam may be activated by the operator, or may be activated automatically when the transport platforms 34 reach a predetermined location on the conveyor mechanism 22.

The X-ray beam is preferably produced as a curtain or fan of X-rays, as described above, so that the vehicle is imaged one cross-section or "slice" at a time as it passes through the inspection area. A collimator mechanism, as described above, is preferably used to narrow and limit the projected beam into a fan of dimensional beams to illuminate the detectors on the frame 12. The collimator mechanism also limits scattering of the X-ray beam off of the vehicle onto the detectors, which may otherwise result in a reduction of contrast in the X-ray images produced.

After the fan of X-ray beams passes through the vehicle, the detectors receive the X-ray beams and produce output signals representative of the individual slices of the vehicle and of the materials located therein. The output signals are sent to an image processor, which sums the output signals together and converts them into a visual image of the vehicle and of the contents contained therein. The visual image of the vehicle and its contents is then sent to a monitor, or other suitable viewing screen, for inspection by the operator.

The operator may then view the images on the monitor to determine whether any improper items are contained within the vehicle. As explained above, dual energy imaging is preferably used to inspect the vehicle such that visual images of metallic materials, organic materials, and inorganic materials located inside the vehicle are readily distinguishable from one another on the monitor. For example, in a preferred dual energy imaging scheme, organic materials, which may be indicative of contraband, may appear as an orange color on the monitor. Metallic materials, conversely, may appear as a blue color. As a result, the system operator is preferably able to readily identify organic materials located inside the vehicle, which is made up of mainly metallic components.

If the operator determines that one or more improper items might be contained within the vehicle, the operator may then exit the operator cabin 13 to physically inspect the vehicle. The operator may first activate the activation mechanism to move the vehicle back onto the first conveyor mechanism 24, which is preferably positioned relatively close to the operator cabin 13, if the operator so desires. Alternatively, one or more vehicle inspectors may be employed to physically inspect vehicles suspected of containing improper items. After physically inspecting the vehicle, the operator and/or inspectors may detain the driver and the vehicle if one or more improper items are found inside the vehicle. If no such items are found, the operator and/or inspectors may then inform the driver that he/she is free to exit the inspection site.

If it is determined by the operator and/or the inspectors that the vehicle being inspected does not contain any improper items, the operator may activate the activation mechanism to move the transport platforms 34 and the vehicle to the far end of the second conveyor section 26 (if the vehicle is not there already). The driver (and any passengers) may then step into the vehicle, without the aid of steps and/or railings due to the minimal height of the conveyor mechanism 22, and drive off of the conveyor mechanism 22 and away from the inspection site.

Once the previously inspected vehicle exits the inspection system 10, the system operator may activate the activation mechanism to rotate the rollers 28 toward the system entrance, such that the transport platforms 34 are moved onto the rollers 28 of the first conveyor section 24 for receiving a new vehicle to be inspected. The described inspection process may then be repeated for the new vehicle. The entire inspection process is preferably performed in less than one minute per vehicle (for vehicles not suspected of containing any improper items), more preferably between 20 and 30 seconds, due to the ease of ingress and egress to and from the vehicle, and the relatively minimal size of the conveyor mechanism 22 in general.

D. Description of an Alternative System Embodiment

Figure 8:
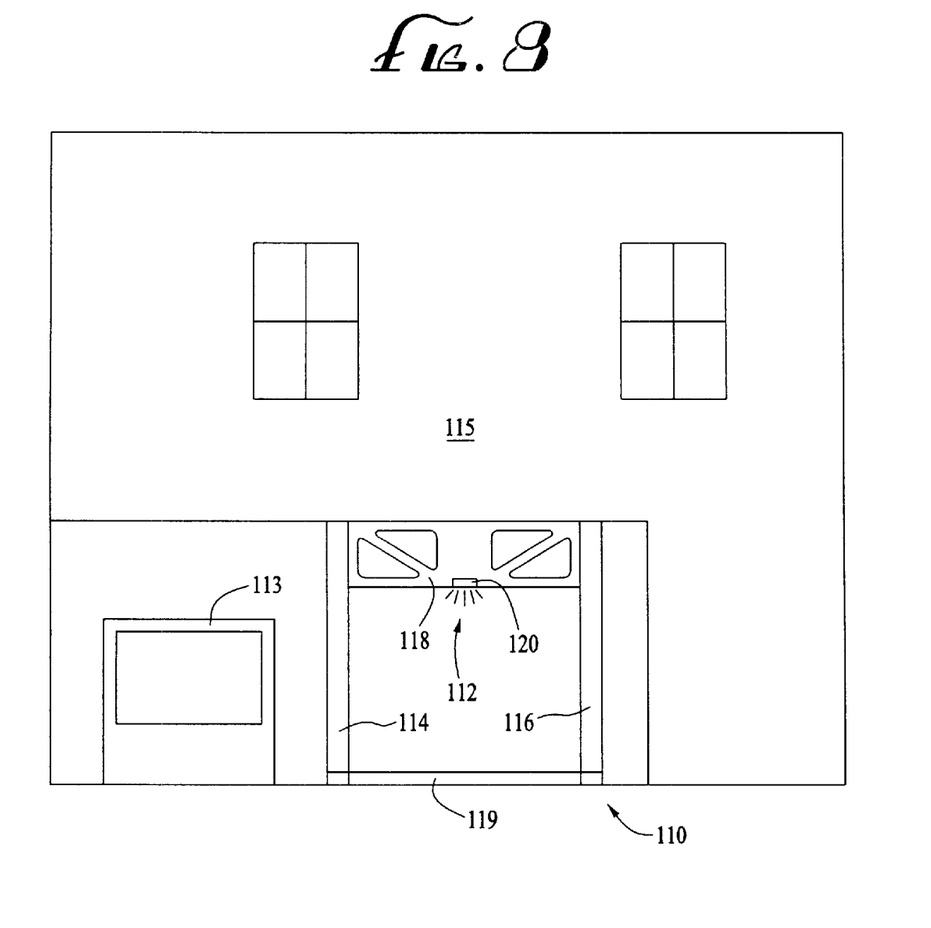
FIG. 8 is a front-sectional view of an alternative embodiment of a relocatable X-ray inspection system located over a building entrance.

FIG. 8 illustrates an alternative embodiment of an X-ray inspection 110, utilizing an X-ray frame 112 that may be installed over the entrance to a building 115 or parking structure. The inspection frame 112 is preferably a substantially rectangular frame that may rest on the ground at the entrance to a building or parking structure entrance.

The X-ray frame 112 is substantially similar to the X-ray frame 12 described above. The frame 112 preferably includes a first leg section 114 connected to a second leg section 116 by an X-ray generator section 118. An X-ray source 120 is preferably disposed on the X-ray generator section 118 for producing X-ray beams, as described above. The X-ray frame 112 further preferably includes a base section 119 that rests on, or is flush with the surface of, the entrance floor. Detectors may preferably be located on the first and second leg sections 114, 116 and the base section 119 of the frame 112.

The frame 112 may be deployed in substantially the same manner as that described for the X-ray frame 12 described in the previous embodiments. Vehicles may be driven over the base section 119 of the frame 112 during inspection. When a vehicle driver enters the building 115 or structure, he/she preferably drives slowly under the X-ray generator section 118 such that the vehicle may undergo X-ray inspection. Thus, the driver preferably does not exit the vehicle when undergoing the X-ray inspection process. Accordingly, the X-ray source 120 preferably produces X-ray beams at extremely minimal radiation levels, such that vehicle drivers (and passengers) are exposed to minimal radiation.

In this embodiment, it is preferred that a device equipped with radar, lidar, or other suitable optical distance measuring equipment, be disposed on the X-ray frame 112 for measuring the actual instantaneous position and/or location of the vehicle as it passes through the inspection area. Such a device allows the system 110 to adjust the X-ray and imaging parameters to accommodate for the potentially non-uniform motion of the vehicle, and to produce an image with minimal distortion.

The radiation levels produced by the inspection system 110 are preferably in the range of 0.05 micro-Sievert to 0.10 micro-Sievert, which is roughly equivalent to the radiation that a person would be exposed to if he/she were exposed to sunlight for approximately five minutes. Thus, the harmful effects of radiation produced in the system 110 are preferably extremely minimal, if existent at all. Dual energy imaging, as described above, may also be used in the system 110, but preferably only at very minimal radiation levels, which preferably do not exceed 0.10 micro-Sievert, and therefore remain within ANSI Standard N43.17 (NCRP Report 116), which outlines safe limits of radiation exposure for humans.

An operator cabin 113, similar to the one described above, may preferably be set up at or near the building entrance. The operator cabin 113 preferably contains a monitor, or other viewing screen, on which the system operator may view the contents of vehicles entering the building or structure. If the operator feels that an improper item might be located in a vehicle being inspected, the operator may exit the operator cabin 113 and physically inspect the vehicle. If one or more improper items are found in the vehicle, the operator may then notify the proper authorities, and the vehicle and its driver may be detained.

Other site accessories, such as radiation shields, a gate attached to the operator cabin, and any other suitable accessories, such as those described herein, may also be set up at the building entrance. The inspection system 110 does not require a conveyor mechanism, because vehicles may be driven under the X-ray frame 112 under their own power. As a result, the inspection system 110 may preferably be loaded onto, and unloaded off of, a delivery vehicle more quickly than a system utilizing a conveyor mechanism.

Thus while embodiments and applications of the present invention have been shown and described, it would be apparent to one skilled in the art that other modifications are possible without departing from the inventive concepts herein. The invention, therefore, is not to be restricted except in the spirit of the claims that follow.

What is claimed is:

1. A relocatable security inspection system, comprising:
    a substantially rectangular frame having first and second substantially vertical leg sections spaced apart from one another by a distance greater than a width of an object to be imaged, the space between the first and second leg sections defining an inspection area;
    a conveyor mechanism connected to the frame for transporting the object through the inspection area, the conveyor mechanism configured to rest on a surface and having a height that permits a vehicle driver to readily step off of the conveyor mechanism onto the surface;
    an X-ray source disposed on the frame for generating an X-ray beam along an outgoing path toward the object while the object moves through the inspection area;
    a detector disposed on the frame in the outgoing path for receiving the X-ray beam after the X-ray beam passes through the object, and for producing an output signal representative of the object and of contents located inside the object;
    an image processor for converting the output signal into a visual image of the object and of the contents located inside the object.

2. The system of claim 1 wherein the detector is disposed on at least one of the first and second leg sections.

3. The system of claim 1 wherein the frame includes a substantially horizontal base section connecting the first and second leg sections, the detector disposed on the base section.

4. The system of claim 1 wherein the frame includes a substantially horizontal X-ray generator section connecting the first and second leg sections, the X-ray source disposed on the X-ray generator section.

5. The system of claim 1 wherein the height of the conveyor mechanism is from one inch to two feet.

6. The system of claim 1 wherein the height of the conveyor mechanism is from five inches to seven inches.

7. The system of claim 1 wherein the conveyor mechanism comprises rollers having a platform resting thereon for supporting a vehicle, the platform movable along the rollers through the inspection area in two directions.

8. The system of claim 7 wherein the conveyor mechanism further comprises an activation mechanism for turning the rollers in the two directions.

9. The system of claim 1 wherein the conveyor mechanism comprises two sections connected to the frame on opposite sides of the frame, the two sections having substantially equal dimensions.

10. The system of claim 1 further comprising a raising mechanism disposed on the frame for raising the frame into an imaging position.

11. The system of claim 10 wherein the raising mechanism includes a drive gear for turning pulleys connected to the first and second leg sections, the pulleys configured to guide cables that raise the frame into the imaging position.

12. The system of claim 1 further comprising a vehicle for transporting the frame and the conveyor mechanism from one location to another.

13. The system of claim 1 further comprising a radiation shield adjacent to the frame for preventing radiation produced by the X-ray beam from escaping the inspection area.

14. The system of claim 1 wherein the first and second leg sections are extendable from a transport height to an imaging height.

15. A readily deployable security inspection system, comprising:
- a substantially rectangular X-ray frame having first and second substantially vertical leg sections spaced apart from one another by a distance greater than a width of an object to be imaged, the space between the first and second leg sections defining an inspection area;
- a first conveyor section detachably connected to the X-ray frame, the first conveyor section having a first transport mechanism disposed thereon for transporting the object into the inspection area, the first conveyor mechanism having a height that permits a vehicle driver to readily step from a vehicle located thereon onto the surface;
- a second conveyor section detachably connected to the X-ray frame, the second conveyor section comprising a second transport mechanism disposed thereon for transporting the object out of the inspection area, the second conveyor section having a height that permits a vehicle driver to readily step off of the surface into a vehicle located thereon.

16. The system of claim 15 wherein the first transport mechanism comprises a first plurality of successively arranged rollers, and the second transport mechanism comprises a second plurality of successively arranged rollers.

17. The system of claim 16 further comprising a transport platform for supporting and transporting the object, the transport platform movable through the inspection area along the first and second plurality of rollers.

18. The system of claim 15 further comprising an X-ray source disposed on the X-ray frame for generating an X-ray beam along an outgoing path toward the object while the object moves through the inspection area.

19. The system of claim 18 wherein the X-ray frame includes a substantially horizontal X-ray generator section connecting the first and second leg sections, the X-ray source disposed on the X-ray generator section.

20. The system of claim 18 further comprising a detector disposed on the X-ray frame in the outgoing path for receiving the X-ray beam after the X-ray beam passes through the object, and for producing an output signal representative of the object and of contents located inside the object.

21. The system of claim 20 further comprising means for converting the output signal into a visual image of the object and of the contents located inside the object.

22. The system of claim 20 wherein the detector is disposed on at least one of the first and second leg sections.

23. The system of claim 20 wherein the X-ray frame includes a substantially horizontal base section connecting the first and second leg sections, the detector disposed on the base section.

24. The system of claim 15 wherein the height of each the first and second conveyor sections is from one inch to two feet.

25. The system of claim 15 wherein the height of each the first and second conveyor sections is from five inches to seven inches.

26. The system of claim 15 wherein the transport platform comprises a radio-transparent plate.

27. The system of claim 15 further comprising an activation mechanism for rotating the first and second plurality of rollers to move the transport platform in two directions.

28. The system of claim 15 further comprising a radiation shield adjacent to the X-ray frame for preventing radiation produced by the X-ray beam from escaping the inspection area.

29. The system of claim 15 wherein the first and second leg sections are extendable from a transport height to an imaging height.

30. The system of claim 15 further comprising a raising mechanism disposed on the X-ray frame for raising the X-ray frame into an imaging position.

31. The system of claim 30 wherein the raising mechanism includes a drive gear for turning pulleys connected to the first and second leg sections, the pulleys configured to guide cables that raise the X-ray frame into the imaging position.

32. A method of inspecting an object, comprising the steps of:
- deploying a frame having an X-ray source disposed thereon onto a surface;
- activating a drive mechanism disposed on the X-ray frame;
- raising the frame on support rods into a substantially upright position via the drive mechanism, the frame defining an inspection area therein;
- attaching a first conveyor section to a first side of the frame, such that the first conveyor section rests on the surface;
- attaching a second conveyor section to a second side of the frame, such that the second conveyor section rests on the surface;
- moving an object to be imaged onto the first conveyor section;
- generating an X-ray beam from the X-ray source into the inspection area;
- transporting the object from the first conveyor section to the second conveyor section such that the object passes through the inspection area wherein the object is penetrated by the X-ray beam;
- detecting the X-ray beam after the X-ray beam penetrates the object.

33. The method of claim 32 further comprising the steps of:

producing an output signal representative of the object and of contents located inside the object after the X-ray beam is detected; and converting the output signal into a visual image of the object and of the contents located inside the object for viewing by an operator.

34. The method of claim 32 further comprising the step of deploying a substantially flat transport platform onto the first conveyor section after the first conveyor section is attached to the frame, the transport platform configured for supporting and transporting the object.

35. The method of claim 34 wherein the step of moving the object onto the first conveyor section comprises moving the object onto the transport platform, and the step of transporting the object comprises moving the transport platform along a first plurality of rollers disposed on the first conveyor section onto a second plurality of rollers disposed on the second conveyor section.

36. The method of claim 35 further comprising the steps of:

moving the object off of the transport platform after the object passes through the inspection area; and moving the transport platform along the second plurality of rollers onto the first plurality of rollers to receive a new object to be imaged.

37. The method of claim 32 further comprising the step of X-ray imaging the object at a plurality of energy levels such that visual images of metallic materials, organic materials, and inorganic materials located inside the object are readily distinguishable from one another.

38. A method of assembling an X-ray inspection system, the inspection system including a frame having first and second leg sections connected by an X-ray generator section, comprising the steps of:

deploying the frame onto a surface, the first and second leg sections each having a winch mechanism disposed thereon;

attaching a first stabilizing support to a first face of each of the first and second leg sections;

activating the winch mechanisms;

hoisting the frame up on support rods via the first and second winch mechanisms until the first stabilizing supports come to rest on the surface, such that the frame is in a substantially upright position;

attaching a second stabilizing support to a second face of each of the first and second leg sections.

39. The method of claim 38 further comprising the step of extending the first and second leg sections to a height that permits passenger vehicles to readily pass underneath the X-ray generator section of the frame, after the frame is hoisted into the substantially upright position.

40. The method of claim 38 wherein the frame includes a base section connecting the first and second leg sections, the method further comprising the step of attaching a first conveyor section to a first side of the base section, such that the first conveyor section rests on the surface adjacent to a first side of the frame.

41. The method of claim 40 further comprising the step of attaching a second conveyor section to a second side of the base section, such that the second conveyor section rests on the surface adjacent to a second side of the frame.

42. A method of assembling an X-ray inspection system, the inspection system including an X-ray frame having first and second leg sections connected by a X-ray generator section, comprising the steps of:

deploying the X-ray frame onto a surface such that a first face of each of the first and second leg sections faces substantially upward, a second face of each of the first and second leg sections faces substantially sideways and outward from the X-ray frame, and a third face of each of the first and second leg sections faces substantially downward against the surface, the first leg section having a first winch mechanism with a first cable disposed thereon and the second leg section having a second winch mechanism with a second cable disposed thereon;

attaching a first stabilizing support to the first face of first leg section, and a second stabilizing support to the first face of the second leg section;

sliding a first support rod through a support guide located on the second face of the first leg section, and a second support rod through a support guide located on the second face of the second leg section, such that a first end of each support rod engages the surface;

attaching a free end of the first cable to a second end of the first support rod, and a free end of the second cable to a second end of the second support rod;

activating the first and second winch mechanisms to hoist the X-ray frame up on the first and second support rods until the first and second stabilizing supports come to rest on the surface;

attaching a third stabilizing support to the third face of the first leg section, and a fourth stabilizing support to the third face of the second leg section;

activating the first and second winch mechanisms to lower the X-ray frame until the third and fourth stabilizing supports come to rest on the surface.

43. The method of claim 42 wherein the X-ray frame includes a base section connecting the first and second leg sections, the method further comprising the steps of attaching a first conveyor section to a first side of the base section, and a second conveyor section to a second side of the base section, such that the first and second conveyor sections rest on the surface.

44. The method of claim 42 further comprising the step of extending the first and second leg sections to a height that permits passenger vehicles to readily pass underneath the X-ray generator section of the X-ray frame, after the third and fourth stabilizing supports come to rest on the surface.

* * * * *